United States Patent
Kwak et al.

(10) Patent No.: US 11,798,686 B2
(45) Date of Patent: Oct. 24, 2023

(54) SYSTEM AND METHOD FOR SEARCHING FOR PATHOLOGICAL IMAGE

(71) Applicant: DEEP BIO INC., Seoul (KR)

(72) Inventors: Tae Yeong Kwak, Seoul (KR); Sang Hun Lee, Seoul (KR); Sun Woo Kim, Seongnam-si (KR)

(73) Assignee: DEEP BIO INC., Seoul (KR)

( * ) Notice: Subject to any disclaimer, the term of this patent is extended or adjusted under 35 U.S.C. 154(b) by 377 days.

(21) Appl. No.: 17/282,775

(22) PCT Filed: Oct. 4, 2019

(86) PCT No.: PCT/KR2019/013083
§ 371 (c)(1),
(2) Date: Apr. 4, 2021

(87) PCT Pub. No.: WO2020/071877
PCT Pub. Date: Apr. 9, 2020

(65) Prior Publication Data
US 2021/0391076 A1     Dec. 16, 2021

(30) Foreign Application Priority Data
Oct. 5, 2018    (KR) .................. 10-2018-0119348

(51) Int. Cl.
*G06K 9/00*     (2022.01)
*G16H 50/20*     (2018.01)
(Continued)

(52) U.S. Cl.
CPC ............. *G16H 50/20* (2018.01); *G06N 3/045* (2023.01); *G06N 3/088* (2013.01); *G06T 7/0014* (2013.01);
(Continued)

(58) Field of Classification Search
CPC ........ G16H 50/20; G16H 30/40; G16H 50/70; G06N 3/045; G06N 3/088; G06T 7/0014;
(Continued)

(56) References Cited

U.S. PATENT DOCUMENTS 10,748,662 B2    8/2020   Jung
2018/0014465 A1   5/2018   Hsieh et al.
(Continued)

FOREIGN PATENT DOCUMENTS

KR    10-1849072    4/2018
KR    10-1880678    4/2018

OTHER PUBLICATIONS

Lee, Yeha et al., Deep Learning-based Feature Extraction for Medical Image Analysis, Journal of the Korean Society of Imaging Informatics in Medicine, 2014, pp. 1-12, vol. 20, No. 1, Republic of Korea.

*Primary Examiner* — Xin Jia
(74) *Attorney, Agent, or Firm* — H.C. Park & Associates, PLC (57) ABSTRACT

A system for searching for a pathological image includes: an autoencoder having an encoder for receiving an original pathological image and extracting a feature of the original pathological image, and a decoder for receiving the feature of the original pathological image extracted by the encoder and generating a reconstructed pathological image corresponding to the original pathological image; a diagnostic neural network for receiving the reconstructed pathological image generated by the autoencoder that has received the original pathological image, and outputting a diagnosis result of a predetermined disease; and a training module for training the autoencoder and the diagnostic neural network by inputting a plurality of training pathological images, each labeled with a diagnosis result, into the autoencoder. The
(Continued)

autoencoder is trained by reflecting the diagnosis result of the reconstructed pathological image output from the diagnostic neural network.

15 Claims, 4 Drawing Sheets

(51) Int. Cl.
  *G16H 30/40* (2018.01)
  *G06N 3/088* (2023.01)
  *G06T 7/00* (2017.01)
  *G06N 3/045* (2023.01)
  *G06F 18/214* (2023.01)

(52) U.S. Cl.
  CPC ......... *G16H 30/40* (2018.01); *G06F 18/2148* (2023.01); *G06T 2207/30081* (2013.01); *G06V 2201/03* (2022.01)

(58) Field of Classification Search
  CPC ...... G06T 2207/30081; G06F 18/2148; G06V 2201/03
  See application file for complete search history.

(56) References Cited

U.S. PATENT DOCUMENTS

| | | | |
|---|---|---|---|
| 2018/0144214 A1* | 5/2018 | Hsieh | G06T 7/0002 |
| 2018/0144466 A1* | 5/2018 | Hsieh | G06T 7/0012 |
| 2018/0027681 A1 | 9/2018 | Isgum et al. | |
| 2019/0057521 A1* | 2/2019 | Teixeira | G06N 3/044 |
| 2019/0223725 A1* | 7/2019 | Lu | G06N 3/044 |

* cited by examiner

SYSTEM AND METHOD FOR SEARCHING FOR PATHOLOGICAL IMAGE

CROSS REFERENCE TO RELATED APPLICATION

This application is a National State Entry of International Application No. PCT/KR2019/013083 filed on Oct. 4, 2019, and claims priority from and the benefit of Korean Patent Application No. 10-2018-0119348 filed on Oct. 5, 2019, each of which is hereby incorporated by reference for all purposes as if fully set forth herein.

BACKGROUND

Field

The present invention relates to a system and method for searching for a pathological image. More specifically, the present invention relates to a system and method capable of searching for other pathological images similar from the aspect of a feature that is effective for disease diagnosis, using an autoencoder in which features effective for disease diagnosis based on pathological images are reflected in training.

Discussion of the Background

One of major tasks performed by pathology or a pathology department is to read a patient's biometric image (e.g., a biological tissue slide of a patient) and perform diagnosis for determining a state or symptom of a specific disease. The diagnosis like this is a method that depends on the experience and knowledge of medical personnel skilled for an extended period of time. A recent trend is that a method of reading a slide image generated by digitally imaging a biological tissue slide, instead of the biological tissue slide, is gradually increasing.

Meanwhile, recently, attempts have been made for automating the tasks such as recognizing or classifying images using a computer system owing to advancements in machine learning. Particularly, attempts have been made to automate diagnosis performed by skilled medical personnel using a neural network (e.g., a deep learning method using a convolution neural network (CNN)), which is a kind of machine learning, and a representative example thereof is image-based disease diagnosis through deep learning using a neural network (e.g., CNN). In addition, an auxiliary means such as a technique of searching for an image having a characteristic similar to that of a corresponding image when a diagnostician diagnoses a disease based on an image may be very useful for disease diagnosis.

Meanwhile, an autoencoder, which is one of the background technologies of the present invention, is to be described. The autoencoder is a neural network structure mainly used in an unsupervised learning methodology, which is a neural network structure used in unsupervised learning for efficient data coding. The autoencoder learns a function that approximates an output value to an input value, extracts a feature of input data through an encoder, and reconstructs an original data through a decoder.

Figure 1:
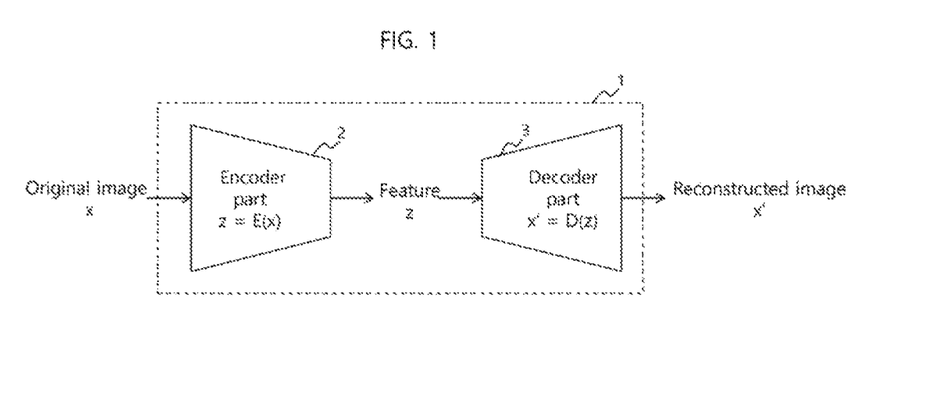
FIG. 1 is a view schematically showing the structure of an autoencoder.

FIG. 1 is a view schematically showing the structure of an autoencoder capable of receiving an image. Referring to FIG. 1, an autoencoder 1 may include an encoder part 2 including a convolutional layer and a decoder part 3 including a deconvolutional layer. When an original image x is input into the encoder 1, encoding is performed on the original image x in the encoder part 2, and a feature ($z=E(x)$) of the original image x is generated. The generated feature z may be decoded in the decoder part 3 to generate a reconstructed image ($x'=D(z)$) corresponding to the original image x.

Since the autoencoder is also a kind of neural network, learning based on a number of training data is preceded, and at the training step of the autoencoder, the following processes are performed on each training data x.

1) Training data x is input into the autoencoder, and reconstructed data x' corresponding to the training data x is generated through an encoding and decoding process.

2) An error $e=L(x, x')$, which is a difference between the training data x and the reconstructed data x', is calculated (L is a loss function).

3) The weighting value in the autoencoder is updated according to the error backpropagation method.

The above information disclosed in this Background section is only for understanding of the background of the inventive concepts, and, therefore, it may contain information that does not constitute prior art.

SUMMARY

Therefore, the present invention has been made in view of the above problems, and it is an object of the present invention to provide a system and method for searching for a pathological image, which can search for other pathological images having a characteristic similar to that of a specific pathological image using an autoencoder.

Additional features of the inventive concepts will be set forth in the description which follows, and in part will be apparent from the description, or may be learned by practice of the inventive concepts.

In addition, another object of the present invention is to provide a system and method for searching for a pathological image, which can search for other pathological images similar from the aspect of a feature that is effective for disease diagnosis by reflecting the effective feature to disease diagnosis based on the pathological images when the autoencoder is trained, and utilizing the autoencoder trained like this.

To accomplish the above objects, according to one aspect of the present invention, there is provided a system for searching for a pathological image, the system including: an autoencoder having an encoder for receiving an original pathological image and extracting a feature of the original pathological image, and a decoder for receiving the feature of the original pathological image extracted by the encoder and generating a reconstructed pathological image corresponding to the original pathological image; a diagnostic neural network for receiving the reconstructed pathological image generated by the autoencoder that has received the original pathological image, and outputting a diagnosis result of a predetermined disease; and a training module for training the autoencoder and the diagnostic neural network by inputting a plurality of training pathological images, each labeled with a diagnosis result, into the autoencoder, wherein the autoencoder is trained by reflecting the diagnosis result of the reconstructed pathological image output from the diagnostic neural network.

In an embodiment, a loss function of the autoencoder may be defined by a difference between the original pathological image and the reconstructed pathological image and a difference between a label of the original pathological image and the diagnosis result of the reconstructed pathological image output from the diagnostic neural network.

In an embodiment, the system for searching for a pathological image may further include a feature generation module for inputting a search pathological image into the trained autoencoder to generate a feature of the search pathological image by the encoder, and storing the generated feature of the search pathological image in a DB, for each of a plurality of search pathological images.

In an embodiment, the system for searching for a pathological image may further include a search module for inputting a query pathological image into the trained autoencoder to generate a feature of the query pathological image by the encoder, and searching for a feature of a similar pathological image similar to the query pathological image from the DB based on the generated feature of the query pathological image.

According to an embodiment of the present invention, the disease may be prostate cancer.

According to another aspect of the present invention, there is provided a system for searching for a pathological image, the system including: an encoder of a trained autoencoder for receiving an original pathological image and extracting a feature of the original pathological image; a database (DB) constructed to include a feature of each of a plurality of search pathological images; and a search module for inputting a query pathological image into the autoencoder to generate a feature of the query pathological image by the encoder, and searching for a feature of a similar pathological image similar to the query pathological image from the DB based on the generated feature of the query pathological image, wherein the autoencoder is trained by the system described above, and the DB is constructed by the system described above.

According to another aspect of the present invention, there is provided a system for searching for a pathological image, the system including: an autoencoder having an encoder for receiving an original pathological image and extracting a feature of the original pathological image, and a decoder for receiving the feature of the original pathological image extracted by the encoder and generating a reconstructed pathological image corresponding to the original pathological image; a diagnostic neural network for receiving the reconstructed pathological image generated by the autoencoder that has received the original pathological image, and outputting a diagnosis result of a predetermined disease; a training module for training the autoencoder by inputting a plurality of training pathological images, each labeled with a diagnosis result, into the autoencoder, and training the diagnostic neural network by inputting a plurality of additional training pathological images, each labeled with a diagnosis result, into the diagnostic neural network, wherein the autoencoder is trained by reflecting the diagnosis result of the reconstructed pathological image output from the diagnostic neural network.

According to another aspect of the present invention, there is provided a method of searching for a pathological image, the method performed by a system including: an autoencoder including an encoder for receiving an original pathological image and extracting a feature of the original pathological image, and a decoder for receiving the feature of the original pathological image extracted by the encoder and generating a reconstructed pathological image corresponding to the original pathological image; and a diagnostic neural network for receiving the reconstructed pathological image generated by the autoencoder that has received the original pathological image, and outputting a diagnosis result of a predetermined disease, the method comprising: a training step of training the autoencoder and the diagnostic neural network by inputting a plurality of training pathological images, each labeled with a diagnosis result, into the autoencoder, wherein the autoencoder is trained by reflecting the diagnosis result of the reconstructed pathological image output from the diagnostic neural network.

In an embodiment, a loss function of the autoencoder may be defined by a difference between the original pathological image and the reconstructed pathological image and a difference between a label of the original pathological image and the diagnosis result of the reconstructed pathological image output from the diagnostic neural network.

In an embodiment, the method of searching for a pathological image may further include a feature generation step of inputting a search pathological image into the trained autoencoder to generate a feature of the search pathological image by the encoder, and storing the generated feature of the search pathological image in a DB, for each of a plurality of search pathological images.

In an embodiment, the method of searching for a pathological image may further include a search step of inputting a query pathological image into the trained autoencoder to generate a feature of the query pathological image by the encoder, and searching for a feature of a similar pathological image similar to the query pathological image from the DB based on the generated feature of the query pathological image.

According to another aspect of the present invention, there is provided a method of searching for a pathological image, the method performed by a system including: an encoder of a trained autoencoder for receiving an original pathological image and extracting a feature of the original pathological image; and a DB constructed to include a feature of each of a plurality of search pathological images, the method including the steps of: inputting a query pathological image into the autoencoder to generate a feature of the query pathological image by the encoder; and searching for a feature of a similar pathological image similar to the query pathological image from the DB based on the generated feature of the query pathological image, wherein the autoencoder is trained by the system described above, and the DB is constructed by the system described above.

According to another aspect of the present invention, there is provided a method of searching for a pathological image, the method performed by a system including: an autoencoder including an encoder for receiving an original pathological image and extracting a feature of the original pathological image, and a decoder for receiving the feature of the original pathological image extracted by the encoder and generating a reconstructed pathological image corresponding to the original pathological image; and a diagnostic neural network for receiving the reconstructed pathological image generated by the autoencoder that has received the original pathological image, and outputting a diagnosis result of a predetermined disease, the method including the steps of: training the autoencoder by inputting a plurality of training pathological images, each labeled with a diagnosis result, into the autoencoder; and training the diagnostic neural network by inputting a plurality of additional training pathological images, each labeled with a diagnosis result, into the diagnostic neural network, wherein the autoencoder is trained by reflecting the diagnosis result of the reconstructed pathological image output from the diagnostic neural network.

According to another aspect of the present invention, there is provided a non-transitory computer-readable storage medium installed in a data processing device and having stored thereon computer executable instructions for performing the methods described above.

According to the concepts of the present invention, there is provided a system and method for searching for a pathological image, which can search for other pathological images having a characteristic similar to that of a specific pathological image using an autoencoder.

In addition, it is possible to provide a system and method for searching for a pathological image, which can search for other pathological images similar from the aspect of a feature that is effective for disease diagnosis by reflecting the effective feature to disease diagnosis based on the pathological images when the autoencoder is trained, and utilizing the autoencoder trained like this.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

As the present invention may apply various modifications and have various embodiments, specific embodiments will be illustrated in the drawings and described in detail in the detailed description. However, this is not intended to limit the present invention to the specific embodiments, and it should be understood to include all modifications, equivalents, and substitutes included in the spirit and scope of the present invention. In describing the present invention, when it is determined that detailed description of a related known technology may obscure the subject matter of the present invention, the detailed description will be omitted.

Although the terms such as "first", "second" and the like may be used to describe various components, the components should not be limited by the terms. These terms are only used for the purpose of distinguishing one component from the other components.

The terms used in the present application are only used to describe specific embodiments, and are not intended to limit the present invention. Singular expressions include plural expressions unless the context clearly indicates otherwise.

In this specification, the terms such as "comprise" or "have" are intended to designate the presence of features, numbers, steps, actions, components, parts, or combinations thereof described in the specification, and it should be understood that they do not preclude the possibility of the presence or addition of one or more other features or numbers, steps, actions, components, parts, or combinations thereof.

In addition, in this specification, when any one component "transmits" data to another component, this means that the component may directly transmit the data to another component, or may transmit the data to another component through at least one other component. On the contrary, when one component "directly transmits" data to another component, it means that the data is transmitted from the component to another component without passing through the other components.

Hereinafter, the present invention will be described in detail focusing on the embodiments of the present invention with reference to the accompanying drawings. The same reference numerals in each drawing indicate the same members.

Figure 2:
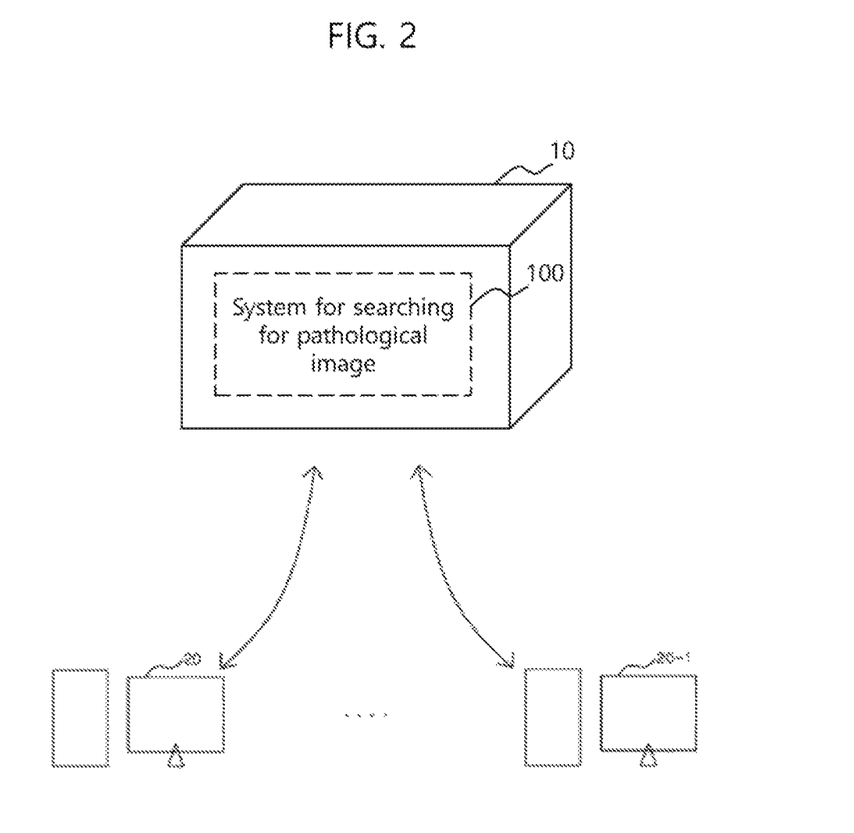
FIG. 2 is a view showing an operating environment of a method of searching for a pathological image according to the concepts of the present invention.

FIG. 2 is a view showing an operating environment of a method of searching for a pathological image according to the concepts of the present invention. Referring to FIG. 2, a method of searching for a pathological image according to the concepts of the present invention may be performed by a system 100 for searching for a pathological image.

The system 100 for searching for a pathological image according to the spirit of the present invention may be installed in a predetermined server 10 to implement the spirit of the present invention. The server 10 means a data processing device having a computing ability for implementing the spirit of the present invention, and those skilled in the art may easily infer that any device capable of performing a specific service such as a personal computer, a portable terminal or the like, as well as a data processing device that can be generally accessed by a client (terminals 20 to 20-1) through a network, may be defined as a server.

The server 10 may include a processor and a storage device. The processor may mean a computing device capable of driving a program for implementing the spirit of the present invention, and may search for a pathological image using the program and an autoencoder defined by the concepts of the present invention. The storage device may mean a data storage means capable of storing programs and various types of data needed for implementation of the concepts of the present invention, and may be implemented as a plurality of storage means according to implementation examples. In addition, the storage device 12 may mean a temporary storage device or a memory that may be included in the processor, as well as a main memory device included in the server 10.

Although it is shown in FIG. 2 that the system 100 for searching for a pathological image is implemented as any one physical device, those skilled in the art may easily infer that the system 100 for searching for a pathological image according to the spirit of the present invention may be implemented by organically combining a plurality of physical devices as needed.

Figure 3:
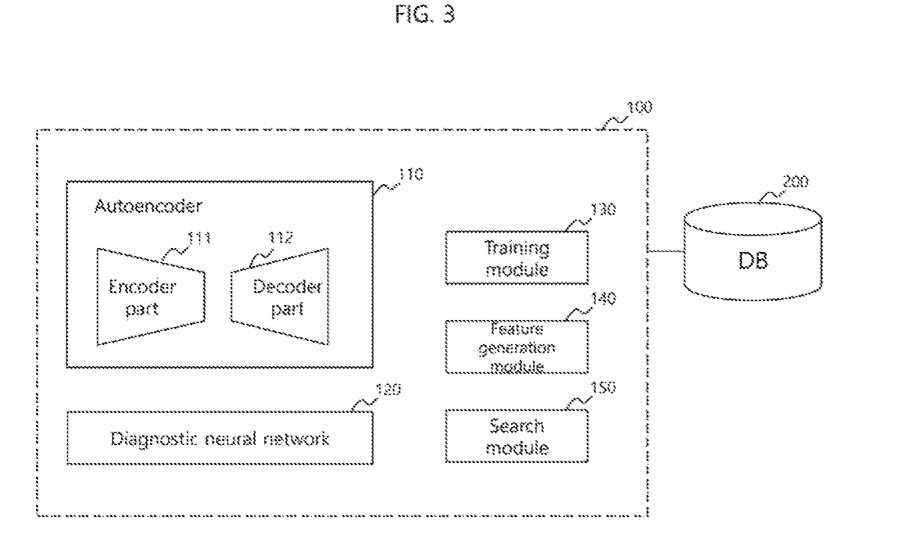
FIG. 3 is a view showing a schematic configuration of a system for searching for a pathological image according to an embodiment of the present invention.

FIG. 3 is a view showing a schematic configuration of a system 100 for searching for a pathological image according to an embodiment of the present invention.

Referring to FIG. 2, the system 100 may include an autoencoder 110, a diagnostic neural network 120, a training module 130, a feature generation module 140, and a search module 150. According to embodiments of the present invention, some components among the components described above may not necessarily correspond to the components essential to implementation of the present invention, and in addition, it goes without saying that the system 100 for searching for a pathological image may include more components according to embodiments. For example, the system 100 may further include a control module (not shown) for controlling functions and/or resources of other components of the system 100 (e.g., the training module 130, the feature generation module 140, the search module 150, and the like). In addition, according to embodiments, the system 100 may further include a database (DB) 200 for storing various types of information and/or data needed for implementation of the concepts of the present invention. Alternatively, according to embodiments, the system 100 may not include the training module 130 and/or the feature generation module 140.

The system 100 may mean a logical configuration provided with hardware resources and/or software needed to implement the spirit of the present invention, and does not necessarily mean a physical component or a device. That is, the system 100 may mean a logical combination of hardware and/or software provided to implement the spirit of the present invention, and may be implemented as a set of logical components if needed by being installed in the devices separated from each other and performing their functions to implement the spirit of the present invention. In addition, the system 100 may mean a set of components separately implemented for each function or role for implementing the spirit of the present invention. For example, the autoencoder 110, the diagnostic neural network 120, the training module 130, the feature generation module 140, and the search module 150 may be located in different physical devices, or may be located in the same physical device. In addition, according to implementation examples, combinations of software and/or hardware configuring each of the autoencoder 110, the diagnostic neural network 120, the training module 130, the feature generation module 140, and the search module 150 may also be located in different physical devices, and components located in different physical devices may be organically combined with each other to implement each of the modules.

In addition, in this specification, a module may mean a functional or structural combination of hardware for performing the spirit of the present invention and software for driving the hardware. For example, those skilled in the art may easily infer that the module may mean a predetermined code and a logical unit of hardware resources for executing the predetermined code, and does not necessarily mean a physically connected code or a single type of hardware.

The DB 200 may store a plurality of pathological images. The pathological images may be various biometric images including tissue images.

According to embodiments, the DB 200 may include a plurality of training pathological images for training the autoencoder 110 and the diagnostic neural network 120 described below. In addition, according to embodiments, the DB 200 may include a plurality of search pathological images. A result of diagnosis on a training pathological image may be labeled in advance on the training pathological image, and the labeled diagnosis result may also be stored in the DB 200 in association with a training pathology data corresponding thereto.

The autoencoder 110 may include an encoder part 111 and a decoder part 112.

The encoder part 111 may receive an original pathological image and extract a feature of the original pathological image.

The decoder part 112 may receive the feature of the original pathological image extracted by the encoder part 111 and generate a reconstructed pathological image corresponding to the original pathological image.

The diagnostic neural network 120 may be a neural network for image-based disease diagnosis. Particularly, the diagnostic neural network 120 may receive the reconstructed pathological image generated by the autoencoder that has received the original pathological image and output a diagnosis result of a predetermined disease.

For example, the disease may be prostate cancer, and although it is described focusing on the prostate cancer hereinafter, those skill in the art may easily understand that the concepts of the present invention is not limited to the prostate cancer.

In this specification, performing a diagnosis may mean making a determination about a specific disease based on a slide or a part thereof (e.g., a patch or a tile), which is a biometric image in which a biological tissue is expressed. Accordingly, a result of diagnosis on the biometric image may include a degree of progression of a specific disease (or a probability corresponding to the degree of progression), in addition to whether or not a specific disease is expressed. For example, when the spirit of the present invention is used for diagnosis of prostate cancer, the Gleason Pattern or the Gleason Score, which are indexes indicating a degree of progression of prostate cancer, may be included in the diagnosis result. For example, the Gleason score has a value of 2 to 5, and generally, a value of 6 to 10 may be regarded as a cancer, and a larger number indicates a higher degree of expression of prostate cancer. The Gleason pattern may be classified into class 1 to 5. Meanwhile, the diagnosis result may include a site where the disease is expressed.

The diagnostic result output from the diagnostic neural network 120 may be diverse according to embodiments. For example, the diagnostic neural network 120 may perform classification for determining existence of a specific symptom (e.g., prostate cancer). Alternatively, according to embodiments, the diagnostic neural network 120 may perform multiple classification or regression estimation for determining severity of a specific symptom (e.g., prostate cancer). Alternatively, the diagnostic neural network 120 may perform multiple classification, regression estimation, or semantic image segmentation to detect a lesion location of a specific symptom.

In this specification, the neural network may mean a set of information expressing a series of design items defining the neural network. In this specification, the neural network may be a convolution neural network.

As is known well, the convolution neural network may include an input layer, a plurality of hidden layers, and an output layer. Each of the plurality of hidden layers may include a convolution layer and a pooling layer (or subsampling layer).

The convolution neural network may be defined by functions, filters, strides, weighting factors or the like for defining each of these layers. In addition, the output layer may be defined as a fully connected feedforward layer.

The design details of each layer constituting the convolution neural network are widely known. For example, known functions or functions separately defined to implement the spirit of the present invention may be used for the number of layers to be included in the plurality of layers and for each of a convolution function, a pooling function, and an activation function for defining the plurality of layers.

An example of the convolution function is a discrete convolution sum. As an example of the pooling function, max pooling, average pooling, or the like may be used. An example of the activation function may be a sigmoid, a tangent hyperbolic (tan h), a rectified linear unit (ReLU), or the like.

When the design items of the convolution neural network are defined, the convolution neural network of which the design items are defined may be stored in the storage device. In addition, when the convolution neural network is trained, a weighting factor corresponding to each layer may be specified.

That is, training of the convolution neural network may mean a process of determining weighting factors of each layer. In addition, when the convolution neural network is trained, the trained convolution neural network may receive an input data through the input layer and output an output data through the previously defined output layer.

The neural network according to an embodiment of the present invention may be defined by selecting any one or a plurality of design items widely known as described above, or independent design items may be defined for the neural network.

The training module 130 may train the autoencoder and the diagnostic neural network by inputting a plurality of training pathological images, each labeled with a diagnosis result, into the autoencoder.

Particularly, the autoencoder is trained by reflecting the diagnosis result of the reconstructed pathological image output from the diagnostic neural network.

In an embodiment, the loss function of the autoencoder 110 may be defined as a form including a difference between the original pathological image and the reconstructed pathological image and a difference between the label of the original pathological image and the diagnosis result of the reconstructed pathological image output from the diagnostic neural network.

For example, the loss function of the autoencoder 110 may be in the form of the following equation.

$$L = w_1 L_1(x,x') + w_2 L_2(y,y') \quad \text{[Equation]}$$

Here, $w_1$ and $w_2$ denote predetermined weighting values, $L_1(a, b)$ and $L_2(a, b)$ denote functions respectively expressing the distance between a and b, x denotes the original pathological image, and x' denotes the reconstructed pathological image corresponding to x, y denotes a label of x, and y' denotes a diagnosis result obtained by diagnosing x' by the diagnostic neural network 120.

Distance functions $L_1$ and/or $L_2$ may include a loss function including a mean squared error (MSE) and a cross entropy error (CEE), or a function expressing a distance between two vectors (e.g., Euclidean distance, n-norm distance, Manhattan distance, etc.). In addition, the two distance functions $L_1$ and $L_2$ may be functions of the same type or different types. In another embodiment, the distance function L may be in the form of the following [Equation] further including an additional term R( ).

$$L = w_1 L_1(x,x') + w_2 L_2(y,y') + R(\ ) \quad \text{[Equation]}$$

Here, R( ) may be a function defined by additional factors such as various parameters of a neural network, an encoding result z, and the like.

Figure 4A:
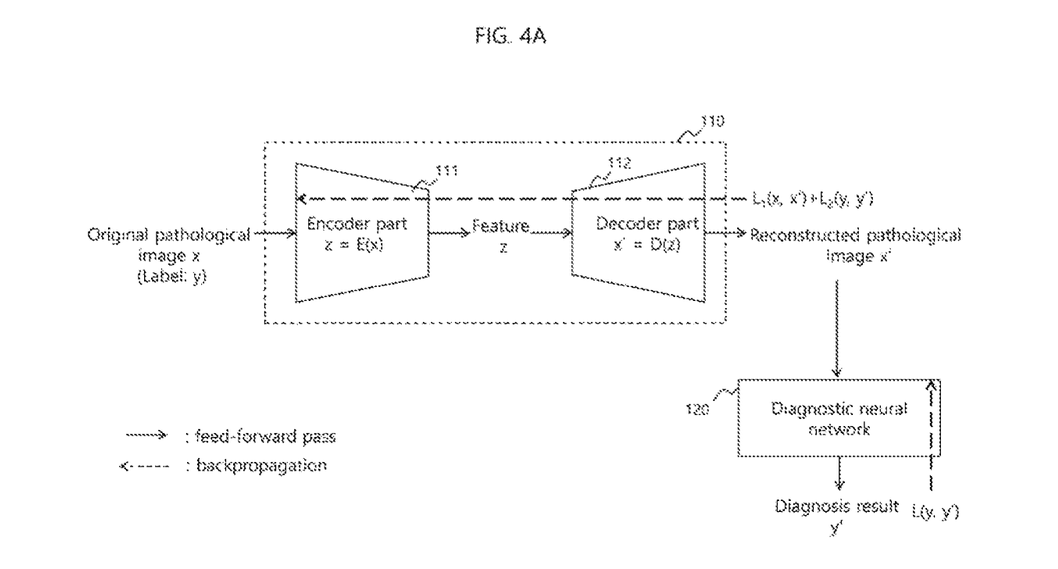
FIGS. 4A, 4B, and 4C are views respectively showing a method of training an autoencoder in a system for searching for a pathological image according to embodiments of the present invention different from each other.

FIG. 4A is a view showing a process in which the autoencoder 110 and the diagnostic neural network 120 are trained by an original pathological image for training.

Referring to FIG. 4A, the feed forward process is as described below.

When the original pathological image x labeled with a diagnosis result y is input into the autoencoder, the feature z of the original pathological image x is generated by the encoder part 111, and the feature z is input into the decoder part to generate a reconstructed pathological image x'. Thereafter, the reconstructed pathological image x' is input into the diagnostic neural network 120, and a diagnosis result y' is output.

In addition, referring to FIG. 4A, the error backpropagation process is performed as shown below.

First, the difference L(y, y') between the diagnosis result y' output from the diagnostic neural network 120 and the label y of the original pathological image x is calculated, and the calculated L(y, y') is reflected to the diagnostic neural network 120 in a backpropagation method. Meanwhile, the diagnosis result y' output from the diagnostic neural network 120 is reflected in the training of the autoencoder 110. For example, as both the difference L1(x, x') between the original pathological image x and corresponding reconstructed image x', and the differences L2(y, y') between the diagnosis result y' output from the diagnostic neural network 120 and the label y of the original pathological image x are reflected to the autoencoder 110 in a backpropagation method, the autoencoder 110 is trained.

Meanwhile, according to embodiments, a plurality of additional training pathological images that have not passed through the autoencoder 110 may be further input into the diagnostic neural network 120 so that training of the diagnostic neural network may be performed. That is, in this embodiment, primarily, the training module 130 may input a plurality of training pathological images into the diagnostic neural network 120 through the autoencoder 110 to train the diagnostic neural network 120, and secondarily, the training module 130 may directly input a plurality of additional training pathological images into the diagnostic neural network 120 without going through the autoencoder 110 to train the diagnostic neural network 120.

Figure 4B:
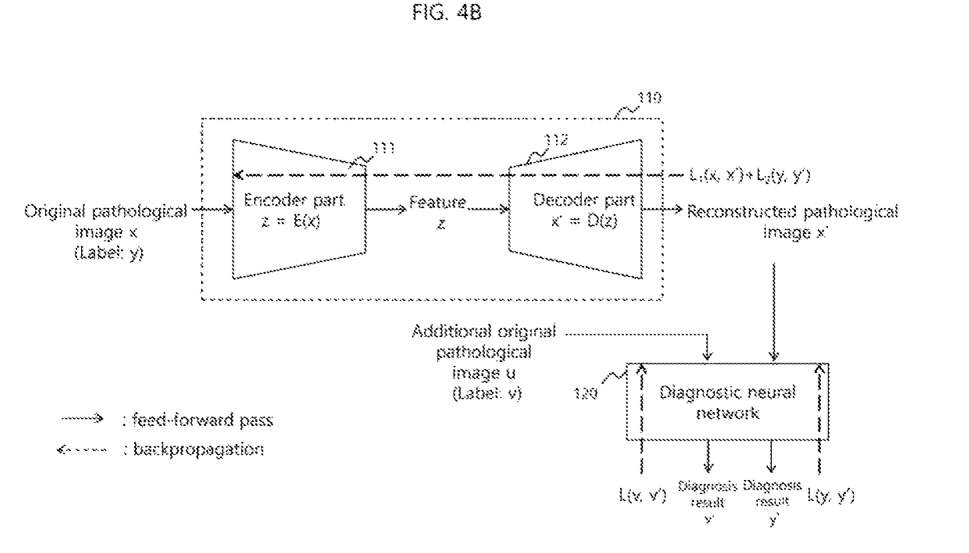

FIG. 4B is a view showing a process of training the autoencoder 110 and the diagnostic neural network 120 according to the above embodiment.

Referring to FIG. 4B, the feed forward process is as described below.

When the original pathological image x labeled with the diagnosis result y is input into the autoencoder 110, feature z of the original pathological image x is generated in the encoder part 111, and the feature z is input into the decoder part to generate reconstructed pathological image x'. Thereafter, the reconstructed pathological image x' is input into the diagnostic neural network 120, and a diagnosis result y' is output. In addition, an additional original pathological image u labeled with diagnosis result v is input into the diagnostic neural network 120, not into the autoencoder 110, and a diagnosis result v' is output.

Referring to FIG. 4B, the error backpropagation process is performed as shown below.

In the case of training by the original pathological image x input into the autoencoder 110, the difference L(y, y') between the diagnosis result y' of the reconstructed image X' output from the diagnostic neural network 120 and the label y of the original pathological image x is calculated, and the calculated L(y, y') is reflected to the diagnostic neural network 120 in a backpropagation method. In addition, the diagnosis result y' output from the diagnostic neural network 120 is reflected in the training of the autoencoder 110. For example, as both the difference L1(x, x') between the original pathological image x and corresponding reconstructed image x', and the differences L2(y, y') between the diagnosis result y' output from the diagnostic neural network 120 and the label y of the original pathological image x are reflected to the autoencoder 110 in a backpropagation method, the autoencoder 110 is trained.

In the case of training by the additional original pathological image u directly input into the diagnostic neural network 120, the difference L(v, v') between the diagnosis result v' output from the diagnostic neural network 120 and the label v of the additional original pathological image u is calculated, and the calculated L(v, v') is reflected to the diagnostic neural network 120 in a backpropagation method.

In this specification, the additional training pathological image or the additional original pathological image means a term for distinguishing the images from the training pathological image or the original pathological image described above (i.e., the pathological image input into the autoencoder 110 and used for training of the autoencoder 110 and the diagnostic neural network 120), and accordingly, a pathological image input into the autoencoder 110 and used for training of the autoencoder 110 and the diagnostic neural network 120 may be referred to as a first training pathological image, and a pathological image directly input into the diagnostic neural network 120 without passing through the autoencoder 110 and used for training of the diagnostic neural network 120 may be referred to as a second training pathological image.

Meanwhile, according to embodiments, before inputting a plurality of first training pathological images into the autoencoder 110 to train the autoencoder 110 and the diagnostic neural network 120, primarily, the training module 130 may train the diagnostic neural network 120 by inputting a plurality of second training pathological images that have not passed through the autoencoder 110 into the diagnostic neural network 120.

In addition, in some cases, there may be an embodiment in which when the diagnostic neural network 120 is trained, the diagnostic neural network 120 is trained only with a plurality of training pathological images directly input into the diagnostic neural network 120 without going through the autoencoder 110.

Figure 4C:
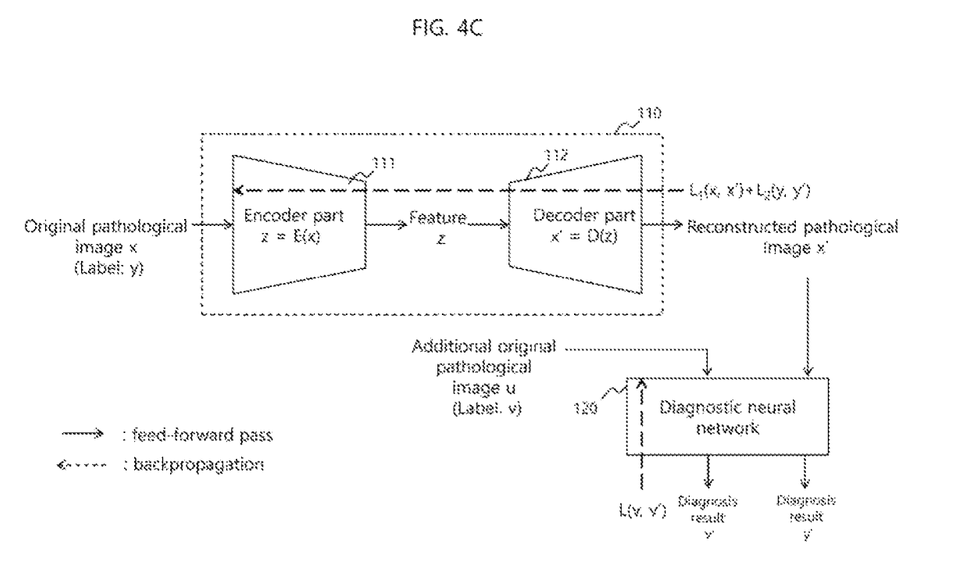
Figure 5:
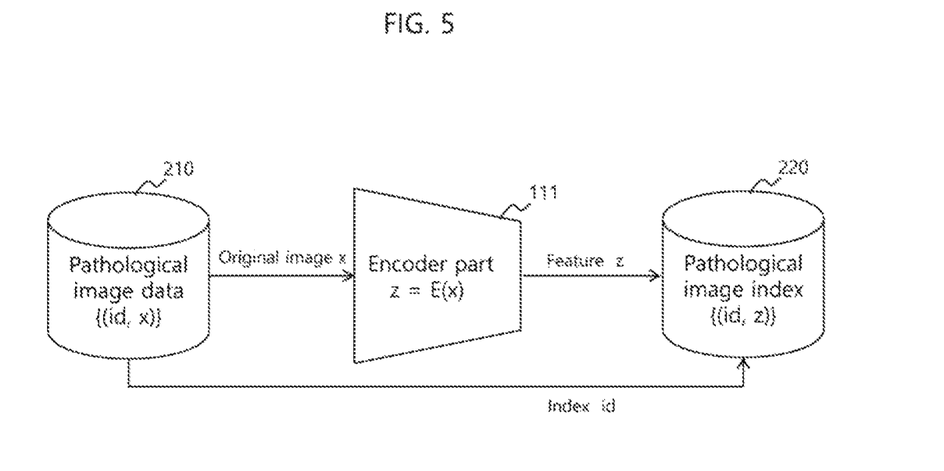
FIG. 5 is a view showing a process of extracting a feature of a search image and constructing a DB in a system for searching for a pathological image according to an embodiment of the present invention.

FIG. 4C is a view showing a process of training the autoencoder 110 and the diagnostic neural network 120 according to the above embodiment.

Referring to FIG. 4C, the feed forward process is as described below.

When the original pathological image x labeled with the diagnosis result y is input into the autoencoder 110, feature z of the original pathological image x is generated in the encoder part 111, and the feature z is input into the decoder part to generate reconstructed pathological image x'. Thereafter, the reconstructed pathological image x' is input into the diagnostic neural network 120, and a diagnosis result y' is output. In addition, an additional original pathological image u labeled with diagnosis result v is input into the diagnostic neural network 120, not into the autoencoder 110, and a diagnosis result v' is output.

Referring to FIG. 4C, the error backpropagation process is performed as shown below.

In the case of training by the original pathological image x input into the autoencoder 110, the difference L(y, y') between the diagnosis result y' of the reconstructed image x' output from the diagnostic neural network 120 and the label y of the original pathological image x is calculated, and the calculated L(y, y') is reflected in the training of the autoencoder 110. For example, as both the difference $L_1(x, x')$ between the original pathological image x and corresponding reconstructed image x', and the differences $L_2(y, y')$ between the diagnosis result y' output from the diagnostic neural network 120 and the label y of the original pathological image x are reflected to the autoencoder 110 in a backpropagation method, the autoencoder 110 is trained.

In the case of training by the additional original pathological image u directly input into the diagnostic neural network 120, the difference L(v, v') between the diagnosis result v' output from the diagnostic neural network 120 and the label v of the additional original pathological image u is calculated, and the calculated L(v, v') is reflected to the diagnostic neural network 120 in a backpropagation method.

Referring to FIG. 3 again, the feature generation module 140 may generate a feature value for each of a plurality of search pathological images after training of the autoencoder 110 is completed, and construct a DB 200 for storing the feature values.

That is, the feature generation module 140 may input the search pathological image into the trained autoencoder 110 to generate a feature of the search pathological image by the encoder part, and store the generated feature of the search pathological image in the DB 200, for each of a plurality of search pathological images.

Figure 6:
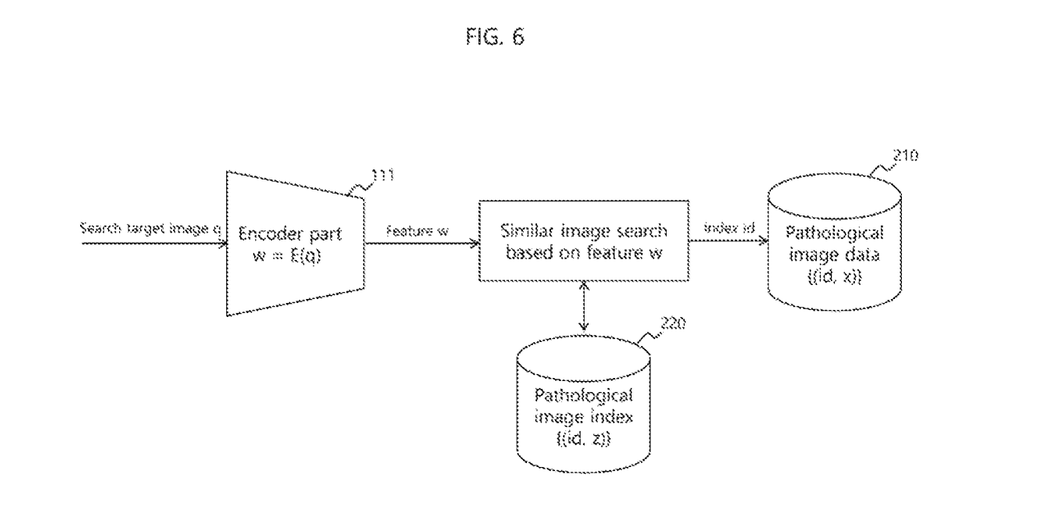
FIG. 6 is a view showing a method of searching for a pathological image in a system for searching for a pathological image according to an embodiment of the present invention.

FIG. 6 is a view showing a process of extracting a feature of each of a plurality of search pathological images and constructing a DB 200, by the feature generation module 140.

Referring to FIG. 6, the DB 200 may include a pathological image data DB 210 and a pathological image index DB 220. The search pathological image may be stored in the pathological image data DB 210 together with an index. For each search pathological image x, the feature generation module 140 may input the search pathological image x into the trained autoencoder 110. Then, the encoder part 111 of the trained autoencoder 110 may extract feature z of the search pathological image x. Then, the feature generation module 140 may link the feature z of the search pathological image x with the index id of the search pathological image x and store them in the pathological image index DB 220.

Meanwhile, referring to FIG. 3 again, after a feature of each of the plurality of search pathological images is extracted, the search module 150 may search for an image similar to a predetermined query pathological image.

Describing this with reference to FIG. 6, the search module 150 may input query pathological image q into the trained autoencoder 110 so that feature w of the query pathological image q may be generated by the encoder part 111.

Thereafter, the search module 150 may search for a feature of a similar pathological image similar to the query pathological image from the DB 200 based on the feature w of the query pathological image q. For example, the search module 150 may perform search based on similarity between the feature of each of a plurality of search pathological images stored in the pathological image index DB 220 and the feature w of the query pathological image q. When the similarity-based search is performed, various techniques for obtaining the similarity between two vectors may be applied. For example, the similarity between two vectors may be expressed by the distance between vectors or cosine similarity, and various known methods may also be applied in addition to this. Meanwhile, when an index id of a similar image similar to the query pathological image q is searched, the search module 150 may search for the similar image from the pathological image data DB 210 using the index.

Meanwhile, according to embodiments, the autoencoder 110 may include a variational autoencoder (VAE).

In addition, although an example of applying the spirit of the present invention to prostate cancer has been mainly described in this specification, those skilled in the art may easily infer that accurate diagnosis is possible when the spirit of the present invention is applied to other cancer or diseases that need diagnosis to be performed on a specific tissue considering the state of surrounding tissues of the tissue, as well as the specific tissue.

Meanwhile, the method of searching for a pathological image according to the concepts of the present invention may be used to more effectively produce training data used for training a machine for diagnosing a disease using a biometric image.

In addition, the method of searching for a pathological image according to the concepts of the present invention may be used to implement a method of diagnosing a pathology through similar image search. For example, a system and method for generating a result of diagnosis on an input slide image may be implemented by converting a specific input slide image to be diagnosed into one or more images that can be searched, performing similar image search on each of the converted images that can be searched, and integrating results of diagnosis on the converted images.

Meanwhile, according to implementation examples, the system 100 and/or the terminal 20 for searching for a pathological image may include a processor and a memory for storing programs executed by the processor. The processor may include single-core CPUs or multi-core CPUs. The memory may include high-speed random-access memory and may include one or more non-volatile memory devices such as magnetic disk storage devices, flash memory devices, and other non-volatile solid state memory devices. Access to the memory by the processor and other components may be controlled by a memory controller.

Meanwhile, the method of searching for a pathological image according to an embodiment of the present invention may be implemented in the form of a computer-readable program command and stored in a non-transitory computer-readable recording medium, and control programs and target programs according to an embodiment of the present invention may also be stored in the computer-readable recording medium. The computer-readable recording medium includes all types of recording devices for storing data that can be read by a computer system.

The program commands recorded in the recording medium may be specially designed and configured for the present invention, or may be known to and used by those skilled in the software field.

Examples of the computer-readable recording medium include magnetic media such as hard disks, floppy disks, and magnetic tapes, optical media such as CD-ROMs and DVDs, magneto-optical media such as floptical disks, and hardware devices specially configured to store and execute program commands, such as ROM, RAM, flash memory and the like. In addition, the computer-readable recording medium may be distributed in computer systems connected through a network to store and execute computer-readable codes in a distributed manner.

Examples of program instructions include high-level language codes that can be executed by a device that electronically processes information using an interpreter or the like, e.g., a computer, as well as machine language codes such as those produced by a compiler.

The hardware device described above may be configured to execute as one or more software modules to perform the operation of the present invention, and vice versa.

The above description of the present invention is for illustrative purposes, and those skilled in the art may understand that it is possible to easily transform into other specific forms without changing the spirit or essential features of the present invention. Therefore, it should be understood that the embodiments described above are illustrative and non-limiting in all respects. For example, each component described as a single form may be implemented in a distributed manner, and in the same manner, components described as being distributed may also be implemented in a combined form.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A system for searching for a pathological image, the system comprising:
an autoencoder including an encoder configured to receive an original pathological image and extract a feature of the original pathological image, and a decoder configured to receive the feature of the original pathological image extracted by the encoder and generate a reconstructed pathological image corresponding to the original pathological image;
a diagnostic neural network configured to receive the reconstructed pathological image generated by the autoencoder that has received the original pathological image, and output a diagnosis result of a predetermined disease; and
a training module configured to train the autoencoder and the diagnostic neural network by inputting a plurality of training pathological images, each labeled with a diagnosis result, into the autoencoder,
wherein the autoencoder is trained by reflecting the diagnosis result of the reconstructed pathological image output from the diagnostic neural network.

2. The system according to claim 1, wherein a loss function of the autoencoder includes a difference between the original pathological image and the reconstructed pathological image and a difference between a label of the original pathological image and the diagnosis result of the reconstructed pathological image output from the diagnostic neural network.

3. The system according to claim 1, further comprising a feature generation module configured to input a search pathological image into the trained autoencoder to generate a feature of the search pathological image by the encoder, and store the generated feature of the search pathological image in a database (DB), for each of a plurality of search pathological images.

4. The system according to claim 3, further comprising a search module configured to input a query pathological image into the trained autoencoder to generate a feature of the query pathological image by the encoder, and search for a feature of a similar pathological image similar to the query pathological image from the DB based on the generated feature of the query pathological image.

5. The system according to claim 1, wherein the disease is prostate cancer.

6. The system according to claim 1, wherein the training module is further configured to input a plurality of additional training pathological images, each labeled with a diagnosis result, into the diagnostic neural network to train the diagnostic neural network.

7. A system for searching for a pathological image, the system comprising:
- an autoencoder including an encoder configured to receive an original pathological image and extract a feature of the original pathological image, and a decoder configured to receive the feature of the original pathological image extracted by the encoder and generate a reconstructed pathological image corresponding to the original pathological image;
- a diagnostic neural network configured to receive the reconstructed pathological image generated by the autoencoder that has received the original pathological image, and output a diagnosis result of a predetermined disease;
- a training module configured to train the autoencoder by inputting a plurality of training pathological images, each labeled with a diagnosis result, into the autoencoder, and train the diagnostic neural network by inputting a plurality of additional training pathological images, each labeled with a diagnosis result, into the diagnostic neural network,
- wherein the autoencoder is trained by reflecting the diagnosis result of the reconstructed pathological image output from the diagnostic neural network.

8. A method of searching for a pathological image, the method performed by a system including:
- an autoencoder including an encoder for receiving an original pathological image and extracting a feature of the original pathological image, and a decoder for receiving the feature of the original pathological image extracted by the encoder and generating a reconstructed pathological image corresponding to the original pathological image; and
- a diagnostic neural network for receiving the reconstructed pathological image generated by the autoencoder that has received the original pathological image, and outputting a diagnosis result of a predetermined disease, the method comprising:
- a training step of training the autoencoder and the diagnostic neural network by inputting a plurality of training pathological images, each labeled with a diagnosis result, into the autoencoder,
- wherein the autoencoder is trained by reflecting the diagnosis result of the reconstructed pathological image output from the diagnostic neural network.

9. The method according to claim 8, wherein a loss function of the autoencoder includes a difference between the original pathological image and the reconstructed pathological image and a difference between a label of the original pathological image and the diagnosis result of the reconstructed pathological image output from the diagnostic neural network.

10. The method according to claim 8, further comprising a feature generation step of inputting a search pathological image into the trained autoencoder to generate a feature of the search pathological image by the encoder, and storing the generated feature of the search pathological image in a database (DB), for each of a plurality of search pathological images.

11. The method according to claim 10, further comprising a search step of inputting a query pathological image into the trained autoencoder to generate a feature of the query pathological image by the encoder, and searching for a feature of a similar pathological image similar to the query pathological image from the DB based on the generated feature of the query pathological image.

12. The method according to claim 9, wherein the training step includes a step of further inputting a plurality of additional training pathological images, each labeled with a diagnosis result, into the diagnostic neural network to train the diagnostic neural network.

13. A method of searching for a pathological image, the method performed by a system including:
- an autoencoder including an encoder for receiving an original pathological image and extracting a feature of the original pathological image, and a decoder for receiving the feature of the original pathological image extracted by the encoder and generating a reconstructed pathological image corresponding to the original pathological image; and
- a diagnostic neural network for receiving the reconstructed pathological image generated by the autoencoder that has received the original pathological image, and outputting a diagnosis result of a predetermined disease, the method comprising the steps of:
- training the autoencoder by inputting a plurality of training pathological images, each labeled with a diagnosis result, into the autoencoder; and
- training the diagnostic neural network by inputting a plurality of additional training pathological images, each labeled with a diagnosis result, into the diagnostic neural network,
- wherein the autoencoder is trained by reflecting the diagnosis result of the reconstructed pathological image output from the diagnostic neural network.

14. A non-transitory computer-readable storage medium installed in a data processing device and having stored thereon computer executable instructions for performing the method of claim 8.

15. A non-transitory computer-readable storage medium installed in a data processing device and having stored thereon computer executable instructions for performing the method of claim 13.

* * * * *